Figure 1:
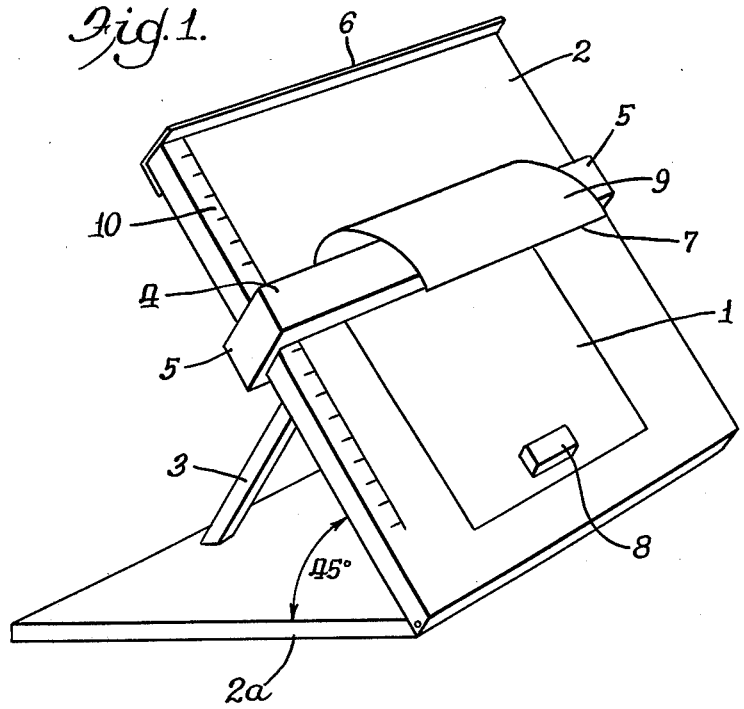

United States Patent [19]
Walter

[11] 4,179,941
[45] Dec. 25, 1979

[54] METHOD OF AND APPARATUS FOR MEASURING THE FLEXURAL STIFFNESS OF A SHEET LIKE SAMPLE

[75] Inventor: Alfred Walter, Schlieren, Switzerland

[73] Assignee: Alfred Walter AG, Schlieren, Switzerland

[21] Appl. No.: 933,997

[22] Filed: Aug. 16, 1978

[30] Foreign Application Priority Data

Aug. 22, 1977 [CH] Switzerland ............... 10285/77

[51] Int. Cl.² ............................................. G01N 3/20
[52] U.S. Cl. ...................................................... 73/854
[58] Field of Search ...................... 73/849, 159, 854

[56] References Cited
U.S. PATENT DOCUMENTS 1,824,395  9/1931  Dantzig et al. ................ 73/854
2,860,510  11/1958  Press ................................ 73/159
3,368,394  2/1968  Pasinski et al. .................. 73/854

*Primary Examiner*—Jerry W. Myracle
*Attorney, Agent, or Firm*—Fitch, Even & Tabin

[57] ABSTRACT

A method of and apparatus for measuring the flexural stiffness of a sheet like sample. The sample is placed on an obliquely positioned surface with its upper edge above a horizontal clamping line. The portion of the sample above the clamping line is of sufficient length so that when it is pivoted forward beyond the vertical the top portion of the sample is freely bent outward. The free clamping length of the sample measured between the top edge and the clamping point is then reduced until the top portion of the sample independently pivots back onto the surface. The residual clamping length thereby obtained is a measurement of the flexural stiffness.

10 Claims, 2 Drawing Figures

METHOD OF AND APPARATUS FOR MEASURING THE FLEXURAL STIFFNESS OF A SHEET LIKE SAMPLE

The invention relates to a method of and apparatus for measuring the flexural stiffness of a sheet like sample, particularly a sheet of paper.

In many sheet processing procedures, the flexural stiffness is an essential characteristic that influences the achievable processing performance. Measuring methods and apparatus are known in the prior art for measuring the flexural stiffness of a sample of the sheet. These known methods, however, are expensive, and the apparatus are complicated, expensive and inappropriate for use by the ordinary worker in the plant. These apparatus are used mainly in laboratories or in engineering offices.

In one known measuring method, a flexural torque or force is applied to the sample and the force necessary to provide a defined deformation is measured. The measuring instrument used for this purpose is expensive, because of its sensitivity, and is delicate. The sample must be cut down to a standard size. To effect the measurement purely in the elastic range and to exclude viscoelastic influences, the defined deformation must be derived from the thickness and expansion properties of the sample.

In another known method, a weight loaded sample, which is coiled on a roller, is deflected through a defined angle and the strain change on the roller is measured. This method has the disadvantage that the defined elastic bending is maintained for a given roller diameter only within a certain range of thickness of the sample.

A very expensive prior art apparatus determines the rigidity by determining the resonance frequency of a clamped-on sample.

In another prior art apparatus, one end of a sample is clamped between two rollers and the rollers are pivoted so that a line through the sample at the clamping line is at a 45° angle to vertical and the length of the sample is adjusted until it sags by its inherent weight or an additional weight may be added to the end of the sample. By pivoting of the clamping rollers by 90° through the vertical, it is determined whether the rigidity of the sample is sufficient to follow this pivoting and then to sag in the other direction. This process must be repeated several times, with changes of the clamping length, to determine the critical length at which the sample is able to just barely follow the pivoting movement.

An object of the present invention is to provide a simple and exact stiffness measuring method and apparatus. Another object of the invention is to provide a method of and apparatus for measuring stiffness of sheet like samples without prior trimming of the sample to a normal or standard size and without conversion of the readings. Still another object is the provision of apparatus for measuring stiffness of sheet like samples which is simple and of low manufacturing costs and yet assures high accuracy of the measurements, is rugged and is safe in operation.

Figure 2:
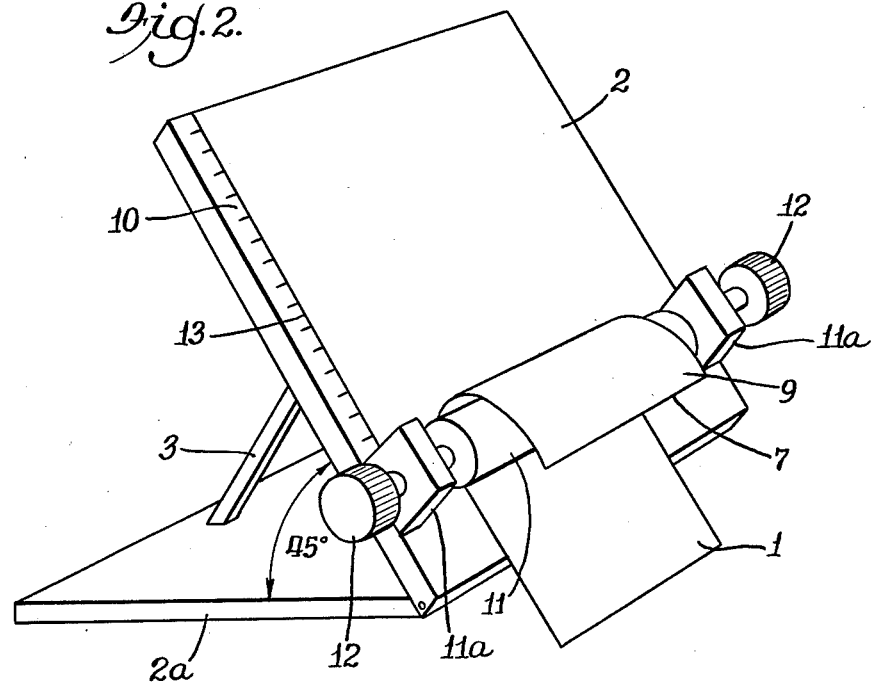

Other objects and advantages of the invention will become apparent by reference to the following description and accompanying drawings wherein:

FIG. 1 is a schematic perspective view of one embodiment of a stiffness measuring apparatus in accordance with the present invention; and FIG. 2 is a schematic perspective view of another embodiment of a stiffness measuring apparatus in accordance with the present invention.

Generally, the measuring method according to the invention includes the steps of placing a sheet like sample on an oblique surface and holding the sample on the surface along a horizontal clamping line so that the upper portion of the sample freely sags about the clamping line. The free clamping length measured between the top edge of the sample and the clamping line is then reduced until the sample independently pivots back onto the oblique surface, whereby the residual clamping length measured at the back pivoting is a measurement of the flexural stiffness of the sample.

For purposes of explanation, the above method will hereinafter be described in connection with apparatus for practicing the method.

As shown in FIG. 1, the apparatus for measuring the flexural stiffness of a sheet like sample, such as a rectangular paper sample 1, includes a rectangular plate 2, which may be made of hard chrome plated steel, having a planar outward facing surface. The plate 2 is mounted at its lower end to a rectangular base 2a, and is positioned obliquely on the base by means of a bracket 3. Preferably, the plate 2 is at a 45° angle with respect to the vertical.

A horizontally extending, elongated measuring rod 4 is disposed in slightly spaced relation to the outward facing surface of the plate 2 by a pair of guide means 5, one at each end of the rod. In the embodiment illustrated in FIG. 1, the measuring rod 4 is a rectangular metal bar and the guide means are U-shaped extensions of the bar which are adapted to slide on the respective sides of the plate. The guide means, which may include cablelines, serrated belts, tooth racks, etc., hold the measuring rod 4 in a vertical position but yet permit the rod to be moved, upward or downward, manually or by means of a motor (not shown). Alternately, the measuring rod may be a roller. An alignment means 6 is provided for aligning the top edge of the sample 1 on the plate 2. In the illustrated embodiment, the alignment means 6 is an elongated L-shaped bar suitably mounted on the upper end of the plate 2 with one leg extending outward of the surface of the plate and parallel to the measuring rod 4. Alternately, the alignment means may be an alignment line scribed in the outer surface of the plate 2.

The sheet like sample 1, whose flexural stiffness is to be measured, is placed on the outward facing surface of the plate 2 with the lower portion of the sample inserted between the plate 2 and the measuring rod 4 and extending below the measuring rod 4. The sample is aligned by pushing its top edge 7 against the alignment bar 6.

As shown in FIG. 1, the lower portion of the sample is held in position on the plate 2 by a holding means 8, which is a permanent magnet. Clamping rods, pins in a soft portion of the plate 2, or pneumatic means may also be used for the holding means 8.

The top edge 7 of the sample 1 is then pivoted forward beyond the vertical so that the upper portion 9 of the sample is bent about the edge of the measuring rod 4, which acts as a clamping line. The length of the sagging sheet portion 9, measured from the top edge of the sample to the edge of measuring rod 4, is called the free clamping length.

Now the measuring rod 4 is moved slowly, by motor or manually, in an upward direction so that the free clamping length of the sample is reduced continuously until its stiffness causes the sample to independently pivot back onto the surface of the plate 2. Alternately, the measuring rod 4 is fixed and the sample is pulled continuously below the rod to reduce the free clamping length. The residual clamping length of the sample is then read by means of a vertical scale 10 scribed on the plate 2 along one lateral margin thereof. Additional scales may be provided, which take into consideration the specific surface weight of the sample and its thickness, so that the stiffness and modulus of elasticity of the sample are read directly. The readings may be determined by electronic means, which senses the position of the measuring rod, and the readings may be printed on the sample by a printer (not shown) operated by the electronic means.

Because atmospheric influences, particularly humidity, can influence the readings, preferably the measuring apparatus is provided with a transparent encapsulation (not shown) to protect the sample.

Due to the fiber structure of the paper, a deformation of the paper takes place under bending, partly elastic by stretching and/or upsetting of the fibers, and partly plastic by pulling the fiber bond apart. Due to the different alignment of the fibers in a sample, the distribution of the tension in a sample is not uniform. Therefore, preferably, the sample is reversed after the first reading and a second reading is made. The mean value of both readings then forms the characteristic value for the flexural stiffness.

The measuring range of the apparatus is relatively large, and the readability is well differentiated, particularly in case of thinner samples. The measurement is carried out automatically in the elastic area of the sample. At higher stiffness values, the measuring range can be expanded by loading the free end of the sample and using corresponding conversions.

The described measuring apparatus is rugged and its operation is simple, which is important for the use in a plant. In most cases the samples need not be cut to size and the reading is not influenced by different dimensions of the samples.

Another embodiment of the measuring apparatus is shown in FIG. 2, wherein parts similar to those of FIG. 1 are indicated with the same reference numerals. In FIG. 2, a horizontal extending, elongated rubber roller 11, which may be similar to a platen roller of a typewriter, is rotatably mounted on the plate 2 in the lower area of the plate 2 by means of bearings 11a for the roller shaft, which bearings are attached to the respective side margins of the plate. The shaft of the roller 11 is mounted in the bearings 11a so as to permit some outward play with respect to the plate 2 to allow for differences in thickness of the various paper samples. The sample 1 is inserted between the roller 11 and the plate 2 and is aligned along a scale edge 13 scribed in the side margin of the plate. By its inherent weight, the roller 11 presses the sample on the plate 2. The roller 11 is manually rotated by the two knurled wheels 12 attached to the respective ends of the shaft of the roller, whereby the sample 1 is pulled beneath it. The sample 1 is pulled downward until the top part 9 of the sample 1 pivots back onto the plate surface. The residual clamping length, which is the distance from the roller axis to the top edge of the sheet 7, is then measured using the scale 10.

The measuring apparatus of FIG. 2 allows for a very accurate and fine measurement. The measuring operation can be facilitated even further by a notching means (not shown) mounted beneath the plate 2 and extending through an opening (not shown) behind the axis of the roller 11 at the left margin of the paper. By pressing a button (not shown), a notch is pressed into the sample at its left margin, adjacent to the measuring scale, and precisely below the axis of the roller 11. The distance from the top edge of the sample to the notch then corresponds with the residual clamping length.

Various other changes and modifications may be made in the measuring apparatus without deviating from the spirit or scope of the present invention. Various features of the invention are set forth in the following claims.

What is claimed is:

1. A method of measuring the flexural stiffness of a sheet like sample comprising placing the sample on an oblique surface with the upper edge being above a horizontal clamping line, pivoting the upper portion of the sample about the vertical so that the upper portion of the sample freely sags outward about the clamping line, and reducing the free clamping length measured between the top edge of the sample and the clamping line until the sample independently pivots back into the oblique surface, whereby the residual clamping length measured at the back pivoting is a measurement of the flexural stiffness of the sample.

2. A measuring method in accordance with claim 1, wherein the portion of the sample below the clamping line is fixed on the oblique surface and the clamping line is shifted relative to the surface upward to reduce the free clamping length.

3. A measuring method in accordance with claim 1, wherein the sample is pulled downward below a stationary clamping line until the residual clamping length is obtained.

4. A method in accordance with any one of the claims 1, 2 or 3 wherein the surface is at a 45 degree angle.

5. An apparatus for measuring the flexural stiffness of a sheet like sample comprising first means for providing a planar obliquely positioned surface, second means for providing a horizontal clamping line on the surface for the sample, third means for changing the free clamping length measured between the upper end of the sample and the clamping line, and fourth means for determining the free clamping length when a sample, which has been pivoted outward of the surface to a position where it freely sags, is pivoted back onto the surface.

6. A measuring apparatus in accordance with claim 5 wherein the surface is inclined by 45° in relation to the vertical.

7. A measuring apparatus in accordance with claim 5 wherein the fifth means is provided for aligning the top edge of the sample parallel with the clamping line.

8. A measuring apparatus in accordance with claim 5 wherein the fourth means is a scale provided on the surface for reading the free clamping length of the sample.

9. A measuring apparatus in accordance with any one of the claims 5, 6, 7 and 8 wherein the second means is moveable along the surface to move the clamping line in a parallel direction.

10. A measuring apparatus in accordance with any one of the claims 5, 6, and 8 wherein the second means is a rotatable roller fixedly mounted on the surface with a slight play perpendicular to the surface, whereby the roller by its inherent weight presses the sample onto the surface.

* * * * *